United States Patent
Aly Hassan et al.

(10) Patent No.: US 12,371,714 B2
(45) Date of Patent: Jul. 29, 2025

(54) CONTINUOUS FLOW REACTOR FOR CONVERSION OF WASTEWATER TO BIOHYDROGEN USING ACTIVATED SLUDGE AND MICROALGAE

(71) Applicant: United Arab Emirates University, Al Ain (AE)

(72) Inventors: Ashraf Aly Hassan, Al Ain (AE); Muhammad Asad Javed, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 18/374,407

(22) Filed: Sep. 28, 2023

(65) Prior Publication Data
US 2025/0109414 A1    Apr. 3, 2025

(51) Int. Cl.
*C12P 3/00* (2006.01)
*C02F 11/02* (2006.01)
(Continued)

(52) U.S. Cl.
CPC .............. *C12P 3/00* (2013.01); *C02F 11/02* (2013.01); *C12M 21/02* (2013.01); *C12M 21/16* (2013.01); *C12M 27/02* (2013.01); *C12M 31/02* (2013.01); *C12N 1/12* (2013.01); *C02F 2209/06* (2013.01); *C02F 2209/22* (2013.01);
(Continued)

(58) Field of Classification Search
CPC ........ C12P 3/00; C02F 11/02; C02F 2209/06; C02F 2209/22; C02F 2209/30; C02F 2209/40; C02F 2305/06; C12M 21/02; C12M 21/16; C12M 27/02; C12N 1/12
See application file for complete search history.

(56) References Cited

U.S. PATENT DOCUMENTS 5,693,537 A * 12/1997 Wilson .................. C12M 23/34
435/297.5
8,246,828 B2    8/2012 Cheong et al.
(Continued)

FOREIGN PATENT DOCUMENTS

CN        108531383 A        9/2018
CN        112707512 A        4/2021
(Continued)

*Primary Examiner* — Michael L Hobbs
*Assistant Examiner* — Lenora A Abel
(74) *Attorney, Agent, or Firm* — Boyle Fredrickson, S.C.

(57) ABSTRACT

Apparatus 101 for producing a continuous stream of biohydrogen includes a continuous flow stirred tank reactor (CSTR) 12, lighting arrangement 13; ports 14; peristaltic pumps 16; and gas chromatograph (GC) 18. The CSTR 12 includes internal bioreactor chamber 20; a photosynthesizing microorganism inlet stream 22.1 for delivering *Chlorella vulgaris*; an organic waste inlet stream 22.2 for delivering wastewater activated sludge (WWAS); and a nutrient inlet stream 22.3 for delivering nutrients into the chamber 20; an outlet stream 24; and stirrers for stirring the contents of the chamber. The lighting 13 is provided by lamps 26 for transmitting light through a transparent sidewall of the chamber 20. The ports 14 and CG 18 are for taking measurements from the chamber 20. The pumps 16 control flowrate of the streams 22.1, 22.2, 22.3 and 24 for regulating biohydrogen production from fermentation while *Chlorella vulgaris* consumes oxygen to avoid biohydrogen conversion into methane.

19 Claims, 6 Drawing Sheets

(51) Int. Cl.
    *C12M 1/00*     (2006.01)
    *C12M 1/06*     (2006.01)
    *C12M 1/16*     (2006.01)
    *C12N 1/12*     (2006.01)

(52) U.S. Cl.
    CPC ...... *C02F 2209/30* (2013.01); *C02F 2209/40* (2013.01); *C02F 2305/06* (2013.01)

(56) References Cited

U.S. PATENT DOCUMENTS

| | | | |
|---|---|---|---|
| 2009/0130704 A1* | 5/2009 | Gyure | C12M 39/00 |
| | | | 435/292.1 |
| 2016/0186072 A1* | 6/2016 | Lehoux | C10G 2/32 |
| | | | 435/167 |
| 2017/0101616 A1 | 4/2017 | Elbeshbishy et al. | |
| 2021/0355419 A1 | 11/2021 | Wang | |

FOREIGN PATENT DOCUMENTS

| | | |
|---|---|---|
| IT | 201800008006 A1 | 2/2020 |
| KR | 10-1809155 B1 | 1/2018 |
| TW | 201109436 A | 3/2011 |
| WO | 2011/071675 A2 | 6/2011 |
| WO | 2012/035410 A2 | 3/2012 |
| WO | 2013/120206 A1 | 8/2013 |
| WO | 2014/152599 A1 | 9/2014 |
| WO | 2015/058295 A1 | 4/2015 |
| WO | 2017/051136 A1 | 3/2017 |
| WO | 2021/229296 A1 | 11/2021 |

\* cited by examiner

CONTINUOUS FLOW REACTOR FOR CONVERSION OF WASTEWATER TO BIOHYDROGEN USING ACTIVATED SLUDGE AND MICROALGAE

FIELD OF INVENTION

This invention relates to a continuous flow reactor for the constant conversion of wastewater to biohydrogen using activated sludge and microalgae.

The present inventors have coauthored the following publication, which is incorporated herein by reference, in its entirety: Javed, Muhammad Asad, and Ashraf Aly Hassan. "Photo Fermentative Biohydrogen Production Potential Using Microalgae—Activated Sludge Co-Digestion in a Sequential Flow Batch Reactor (SFBR)." RSC Advances 12(46): 29785-92 (Oct. 17, 2022).

BACKGROUND TO INVENTION

Hydrogen is a clean and sustainable energy source that can be produced using biological, chemical, and electrochemical pathways. Hydrogen produces only water during the combustion process with no greenhouse gas emissions. Moreover, the standard combustion heat 33.817 Mcal/kg is significantly higher than other natural and fossil fuels.

However, most of the hydrogen produced today is from energy intensive processes such as steam methane reforming and electrolysis. To transition to a more sustainable way, in the 1970s and 1980s, researchers identified several microorganisms such as bacteria and microalgae capable of producing hydrogen gas through metabolic activities. These metabolic activities include mainly anaerobic fermentation and biophotolysis and hydrogen produced through these processes is known as biohydrogen. The discovery laid the foundation for a paradigm shift from fossil fuels to sustainable and clean energy sources such as biohydrogen. Today, natural gas comprises 48% of the world's hydrogen energy generation followed by oil (30%), coal (18%), and water splitting (4%). However, in the recent era, the biohydrogen production via anaerobic fermentation using organic waste and microalgae has gained attention. The main disadvantage of using other thermo and electrochemical pathways is high energy consumption process resulting in expensive price (5.46-7.24 \$/kg) at consumer end. The cost for biohydrogen production via fermentation lies around 7.54 \$/kg which is also expensive due to the use of expensive fermentative products such as sugars and other organic waste. A need exists for a cheaper means of producing biohydrogen. More specifically, a need exists for producing a continuous stream of biohydrogen.

In this specification, the term "continuous stream of biohydrogen" shall be interpreted to mean that the stream is not produced in batches, but is rather produced on an ongoing or continuous basis, no matter how small the amount produced.

SUMMARY OF INVENTION

According to one aspect of the invention, there is provided a method and apparatus for producing biohydrogen using a co-culture of organic waste sludge and photosynthesizing microorganisms to generate a stream of biohydrogen in a continuous flow reactor. The stream of biohydrogen may be a continuous stream of biohydrogen.

According to another aspect of the invention, there is provided an apparatus and method for producing biohydrogen using organic waste sludge and photosynthesizing microorganisms to reduce greenhouse emissions whilst producing biohydrogen.

According to yet another aspect of the invention there is provided an apparatus for producing a stream of biohydrogen, the apparatus including:
 a bioreactor having:
  (a) an internal bioreactor chamber;
  (b) three separate inlet streams, each inlet stream leading into the bioreactor chamber; and
  (c) an outlet stream leading out of the bioreactor chamber and through which the contents of the bioreactor chamber can flow out of the bioreactor chamber;
 fluid flow controlling means for independently controlling a fluid flow through the associated inlet stream for controlling fluid flow via the associated inlet stream into the bioreactor chamber;
 wherein the inlet streams comprise:
  (i) a photosynthesizing microorganism inlet stream;
  (ii) an organic waste inlet stream; and
  (iii) a nutrient inlet stream;
 and lighting means for exposing the photosynthesizing microorganism to light, thereby to enable photosynthesis.

In an example, the photosynthesizing microorganism inlet stream is a microalgae inlet stream.

In an example, the organic waste inlet stream is an activated sludge inlet stream.

In an example, the nutrient stream is a nutrient and carbon substrate.

The stream of biohydrogen may be a continuous stream of biohydrogen.

The bioreactor may comprise a stirring means for stirring the contents of the bioreactor chamber.

The stirring means may be configured for stirring the contents of the bioreactor chamber. The stirring means may be in the form of one or more magnetic stirrers for stirring the contents of the bioreactor chamber. In a particular embodiment the stirrers may be in the form of two pairs of magnetic stirrers. The bioreactor may be in the form of a continuous flow stirred tank reactor (CSTR).

The photosynthesizing microorganisms may be in the form of microalgae. More specifically, in one example the microalgae is *Chlorella vulgaris*. More specifically, the photosynthesizing microorganism inlet stream may be sourced from an outdoor pond.

The organic waste sludge may be in the form of wastewater activated sludge (WWAS). The organic waste sludge may be in the form of any fluid or effluent including food or other organic waste.

The apparatus may include one or more ports in flow communication with the bioreactor chamber. Said one or more ports may be selected from the group consisting of: a pH control port, a hydrogen sensor port, an oxygen sensor port, a gas collection port, a gas sensor port; and combinations thereof.

In some examples, the one or more ports may be provided together in a combination port. For example, the gas collection port and gas sensor port may be provided together in a single port. In other words, the gas collection port may comprise a gas sensor.

The fluid flow controlling means may further include means for controlling a fluid flow through the outlet stream for controlling fluid flow via the outlet stream out of the bioreactor chamber.

As such, the fluid flow controlling means may include one or more of a photosynthesizing microorganism inlet stream controller; an organic waste inlet stream controller; a nutrient inlet stream controller; and an outlet stream controller; for controlling, respectively, a fluid flow through the photosynthesizing microorganism inlet stream; the organic waste inlet stream; the nutrient inlet stream; the outlet stream. As such, the fluid flow controlling means may be operable for controlling one or more of the hydraulic retention time; and the flow rates through the bioreactor.

The or each stream controller may be in the form of a pump. More particularly, each pump may be in the form of a peristaltic pump. As such, the photosynthesizing microorganism inlet stream controller; the organic waste inlet stream controller; the nutrient inlet stream controller; and the outlet stream controller may be in the form of a photosynthesizing microorganism inlet pump; an organic waste inlet pump; a nutrient inlet stream pump; an outlet stream pump.

In a particular embodiment, the lighting means may be provided by a light transmittable sidewall defining the bioreactor chamber, and through which light may enter the bioreactor chamber. The lighting means may further include one or more light sources arranged for transmitting light via the light transmittable sidewall into the interior of the bioreactor chamber. The light sources may be in the form of lamps. The light transmittable sidewall may be in the form of a transparent sidewall.

The apparatus may include a gas chromatograph (GC). The gas chromatograph may employ a thermal conductivity detector (TCD).

The invention may extend to the apparatus defined and described hereinabove including the inlet streams. The invention may extend also to the use of the apparatus defined and described hereinabove.

According to still another aspect of the invention there is provided a method for producing a stream of biohydrogen, the method including:
 providing a bioreactor including an internal bioreactor chamber;
 providing and controlling three separate inlet streams leading into the bioreactor chamber, wherein each separate inlet stream includes:
  (i) a photosynthesizing microorganism inlet stream;
  (ii) an organic waste inlet stream; and
  (iii) a nutrient inlet stream;
 providing and controlling an outlet stream leading out of the bioreactor chamber, exposing the photosynthesizing microorganism to light, thereby to enable photosynthesis.

The method may include providing a stirring means for stirring the contents of the bioreactor chamber.

The stream of biohydrogen may be a continuous stream of biohydrogen.

Providing a bioreactor may comprise providing a continuous flow stirred tank reactor (CSTR).

The photosynthesizing microorganisms may be provided in the form of microalgae. More specifically, the microalgae may be provided in the form of *Chlorella vulgaris*. More specifically, the inlet stream may be sourced from an outdoor pond.

The organic waste sludge may be provided in the form of wastewater activated sludge (WWAS). The organic waste sludge may be provided in the form of any fluid or effluent including food or other organic waste.

The method may include providing one or more ports in flow communication with the bioreactor chamber. Said one or more ports provided may be selected from the group consisting of: a pH control port, a hydrogen sensor port, an oxygen sensor port, a gas collection port, a gas sensor port; and combinations thereof.

The method may include controlling the hydraulic retention time.

The method may further include controlling the flow rates through the bioreactor.

More specifically, the method may include controlling a ratio of *Chlorella vulgaris* to WWAS such that the ratio is 1:1.5.

BRIEF DESCRIPTION OF DRAWINGS

Further features of the invention are described hereinafter by way of a non-limiting example of the invention, with reference to and as illustrated in the accompanying schematic drawings. In the drawings.

DETAILED DESCRIPTION OF THE DRAWINGS

With reference to the drawings, an apparatus for biohydrogen production, in accordance with the invention, and a method for biohydrogen production, in accordance with the invention, is indicated generally by the reference numerals 101 and 100, respectively.

Broadly speaking, the method 100 and the apparatus 101 is configured generally for producing a continuous stream of biohydrogen using a co-culture of organic waste sludge and photosynthesizing microorganisms to generate a stream of biohydrogen in a continuous flow reactor. The method 100 and the apparatus 101 is further configured for producing biohydrogen using organic waste sludge and photosynthesizing microorganisms to reduce greenhouse emissions whilst producing biohydrogen.

The method 100 shall be understood from the configuration and operation of the apparatus 101 described and defined hereinbelow.

The apparatus 101 is specifically configured for producing a continuous stream of biohydrogen from co-cultured microorganisms including photosynthesizing microorganisms in the form of microalgae, specifically, *Chlorella vulgaris* sourced from an outside pond; and organic waste sludge in the form of wastewater activated sludge (WWAS). The applicant has found that in other embodiments, not shown, the organic waste sludge may alternatively, be any fluid or effluent including food or other organic waste.

The apparatus 101 includes a bioreactor in the form of a continuous flow stirred tank reactor (CSTR) 12; lighting means in the form of lighting arrangement 13; ports 14; fluid flow controlling means in the form of peristaltic pumps 16; and gas chromatograph (GC) employing a thermal conductivity detector (TCD) 18; the purpose of which will be explained hereinbelow.

Figure 2:
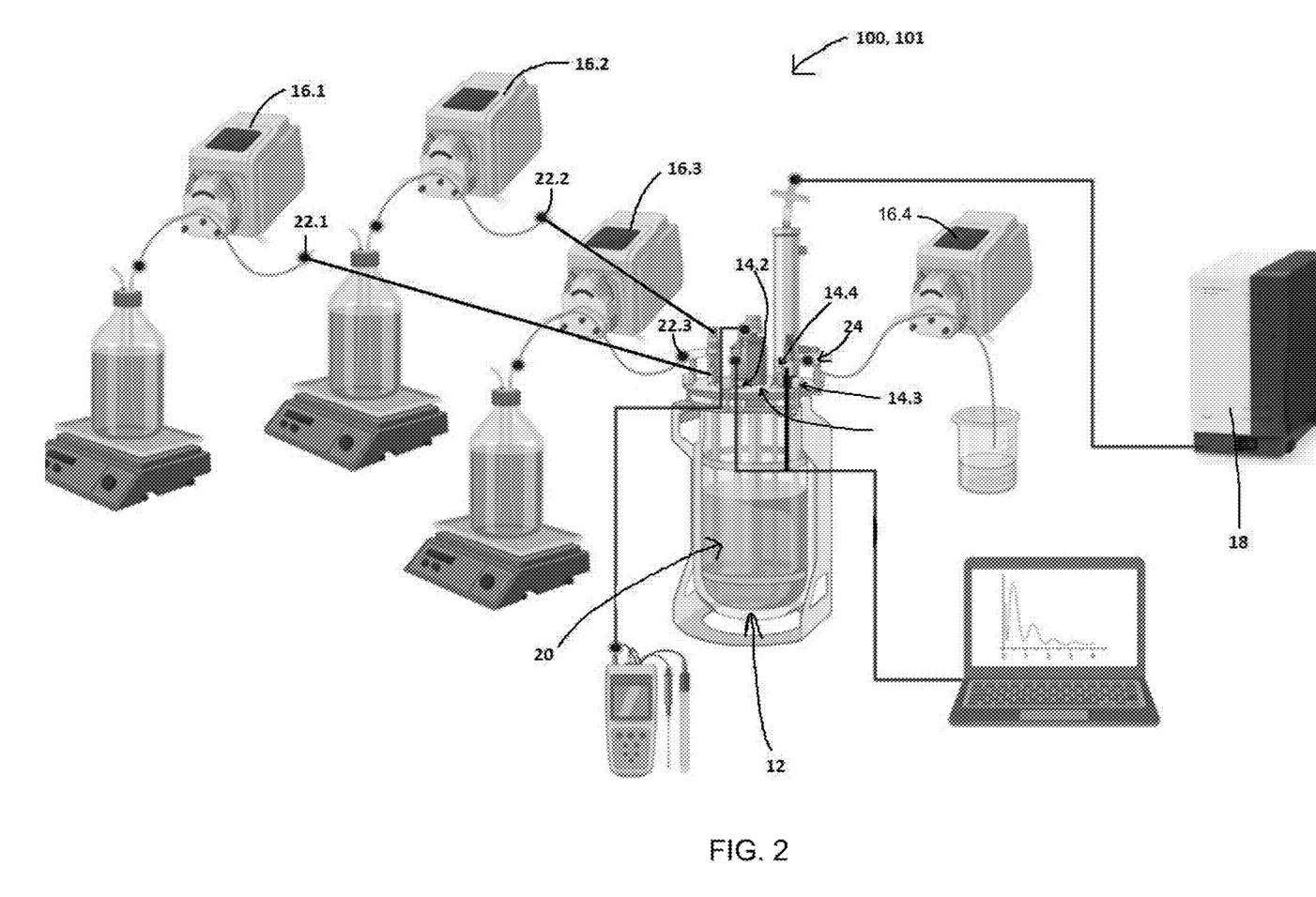
FIG. 2 shows a schematic diagram showing an apparatus, in accordance with an apparatus and method of the invention, for biohydrogen production.

With reference to FIG. 2, the continuous flow stirred tank reactor (CSTR) 12 includes an internal bioreactor chamber 20; three separate inlet streams 22 leading into the bioreactor chamber 20; an outlet stream 24 leading out of the bioreactor chamber and through which the contents of the bioreactor chamber can flow out of the bioreactor chamber 20; and stirring means in the form of two pairs of magnetic stirrers (not shown) for stirring the contents of the bioreactor chamber.

The bioreactor chamber 20 has a sidewall constructed from a transparent, light permeable material such as, for example, glass, or a rigid and transparent thermoplastics material, such as, for example, acrylic, PMMA or Perspex®. In other examples, the bioreactor chamber 20 could be constructed with only portions of the chamber defining walls being light permeable material. For instance, the chamber 20 could have steel walls and a light permeable roof.

As illustrated in FIG. 2 of the drawings, the inlet streams 22 include a photosynthesizing microorganism inlet stream 22.1; an organic waste inlet stream 22.2; and a nutrient inlet stream 22.3. It will be noted that 22.1, 22.2 and 22.3 are indicated by a dot. Whilst the dot of 22.3 is shown on the CSTR 12, it will be understood that although the dots designated by 22.1 and 22.2 are illustrated as "hanging in mid-air", these dots represent connection points leading into the internal bioreactor chamber 20 of the CSTR 12 as described hereinabove.

The photosynthesizing microorganism inlet stream 22.1 is configured for delivering *Chlorella vulgaris* to the bioreactor chamber 20. The organic waste inlet stream 22.2 is configured for delivering WWAS to the bioreactor chamber 20. The nutrient inlet stream 22.3 is configured for delivering nutrients to the bioreactor chamber 20. The outlet stream 24 is configured for delivering the mixture from the bioreactor chamber 20, out of the bioreactor chamber 20.

The lighting arrangement 13 is provided by the transparent sidewall of the bioreactor chamber 20 and lamps 26 arranged for transmitting light through the transparent sidewall of the bioreactor chamber 20 so as to expose the photosynthesizing microorganism (*Chlorella vulgaris*) to light, thereby to enable photosynthesis.

The ports 14 include a pH control port 14.1, a hydrogen sensor port 14.2, an oxygen sensor port 14.3, a gas collection port 14.4,. The ports 14.1, 14.2, 14.3, 14.4, are in flow communication with the bioreactor chamber 20. In this example, the gas collection port comprises a gas sensor. In other examples, the ports may include a separate gas sensor port.

The peristaltic pumps 16 include a photosynthesizing microorganism inlet pump 16.1; an organic waste inlet pump 16.2; a nutrient inlet stream pump 16.3; an outlet stream pump 16.4. As will be explained in more detail hereinbelow, the pumps 16.1, 16.2, 16.3, 16.4 are operable for controlling the hydraulic retention time and the flow rates through the CSTR 12. More specifically, each pump 16.1., 16.2, 16.3, 16.4 is independent and able to control the volume of photosynthesizing microorganism, organic waste and nutrients delivered to the bioreactor chamber 20.

The gas chromatograph (GC) 18 is configured for analysing gas released within the bioreactor chamber 20, as will be explained in more detail hereinbelow.

Experimental Procedure and Results

*Chlorella vulgaris* (CCALA256) was selected as the representative species of microalgae, and was obtained in agar media from CCALA, a culture collection laboratory, in Czech Republic (http://ccala.butbn.cas.cz/).

Figure 1:
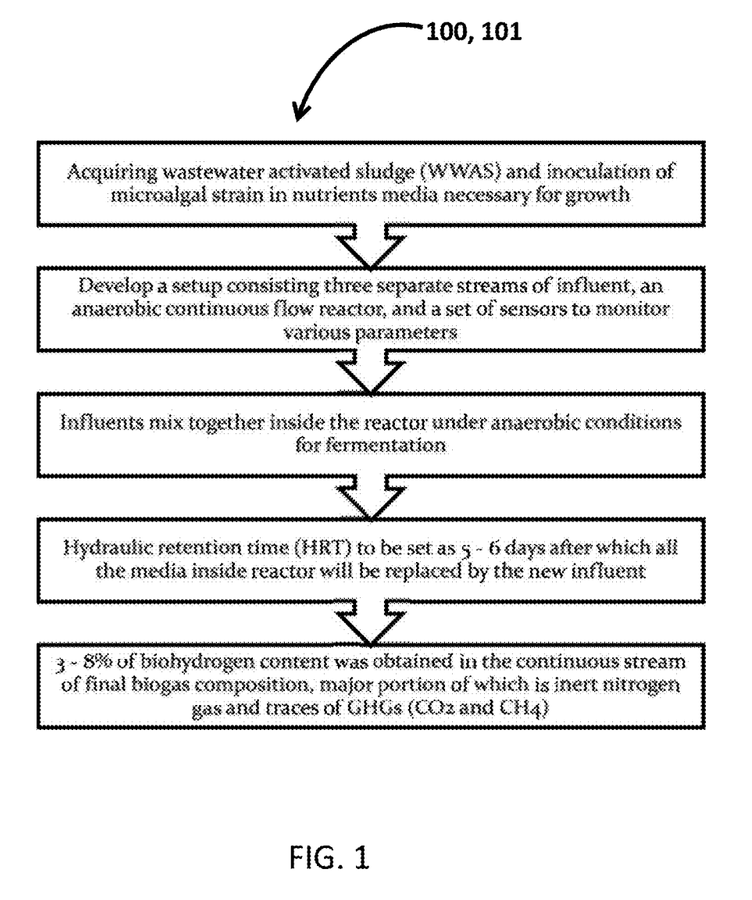
FIG. 1 shows a schematic block diagram of biohydrogen production, in accordance with an apparatus and method of the invention, using a continuous flow stirred tank reactor (CSTR)

The domestic wastewater activated sludge (WWAS) was acquired from Al Saad wastewater treatment plant in Al Ain city, UAE. The WWAS includes a diverse community of microorganisms, including bacteria, protozoa, filamentous bacteria, algae and fungi. However, to prevent the microbial community, especially algae and fungi, from changing its composition prior to use, the activated sludge was stored in a nontransparent container in a refrigerator. The WWAS was used as is, without isolating the bacterial community. To minimize the major microbiological changes in composition and characteristics, the shelf life of activated sludge was limited to one month. The methodology followed during the research work is illustrated as shown in FIG. 1.

Gas Composition Analysis

The gas composition was determined by gas chromatography using a thermal conductivity detector (TCD) based 490 Micro gas chromatograph (GC) 18 (Agilent Technologies Inc., CA, USA). Micro GC was equipped with argon, an inert gas, as the carrier gas operated with 20 m Molsieve 5A and 10 m PoraPLOT Q columns. A standard GC method was established to detect hydrogen ($H_2$), nitrogen ($N_2$), oxygen ($O_2$), and methane ($CH_4$) at a retention time of 1.5, 1.8, 2.3, and 3.7 min, respectively, using a 20 m Molsieve 5A column. Carbon dioxide ($CO_2$) was detected at a retention time of 1.0 min in a second column (10 m PoraPLOT Q column).

The method developed to run the Micro GC was set to take injections at column and injector temperatures of 80° C. and 50° C., respectively. Performance evaluation of CSTR producing biohydrogen: The performance of CSTR 12 was evaluated on the basis of biohydrogen production in the final gas composition. The percentage of different gases ($H_2$, $O_2$, $N_2$, $CH_4$, $CO_2$) depends upon the type and concentration of carbon substrates and nutrients along with co-culture mixing ratio, hydraulic retention time (HRT), flow rates of influent and effluents, and dissolved oxygen (DO). Carbon substrates are sugars usually in the form of glucose measured in mg/L or ppm. The nutrient media (introduced via the nutrient inlet stream 22.3) includes sodium nitrate ($NaNO_3$), calcium nitrate tetrahydrate ($Ca(NO_3)_2.4H_2O$), dipotassium hydrogen phosphate ($K_2HPO_4$), magnesium sulfate heptahydrate ($MgSO_4.7H_2O$), sodium carbonate ($Na_2CO_3$), Fe-EDTA solution, and trace metal solution. Other performance evaluators include an optimized ratio of WWAS (introduced via the organic waste inlet stream 22.2) and microalgae that is to be introduced in the reactor continuously (via the microorganism inlet stream 22.1).

A best performing ratio of 1:1.5 v/v (microalgae: WWAS) was exploited during CSTR 12 operation. A reactor of 1 L capacity was operated with a continuous flow of 200 mL/day as an influent and effluent while maintaining the HRT of 5 days. The concentration of dissolved oxygen in the medium inside CSTR 12 also plays a vital role in triggering the conversion of biohydrogen into methane. As the dissolved oxygen comes from the microalgal partner in co-culture which can be enhanced or reduced by controlling microalgal concentration in the influent.

Experimental Setup

The inventors believe that it is highly advantageous to use a CSTR 12 with three separate influent streams, namely the organic waste inlet stream 22.2 delivering WWAS, the microorganism inlet stream 22.1 delivering *Chlorella vulgaris*, and the nutrient inlet stream 22.3 delivering nutrients. It is further highly advantageous to utilize organic carbon of the WWAS as substrate. More specifically, as the WWAS is a waste product, it can be acquired at no cost and thus can greatly reduce the cost of biohydrogen production.

Figure 3:
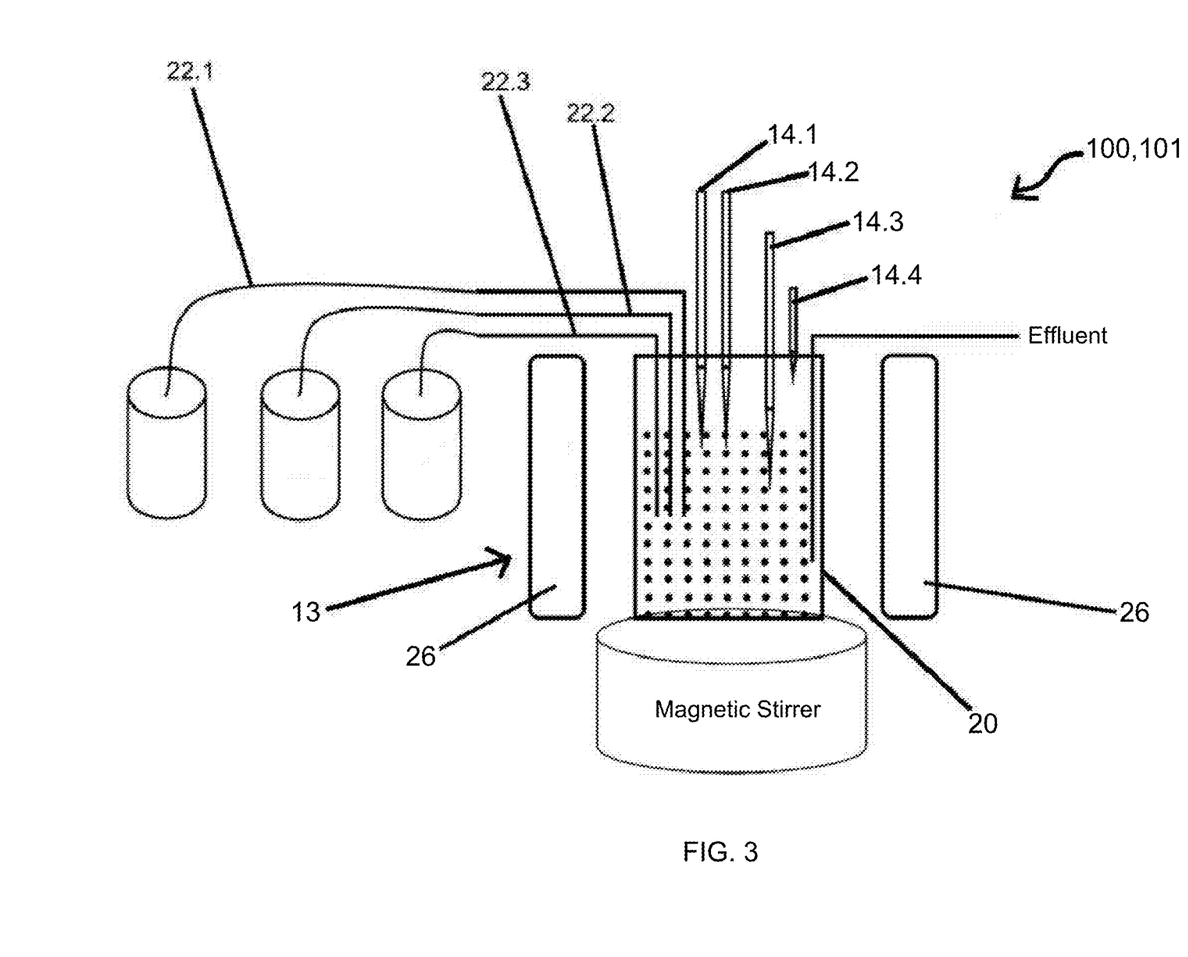
FIG. 3 shows an apparatus, in accordance with an apparatus and method of the invention, in the form of a real-time lab-scale setup of biohydrogen production apparatus.

FIG. 2 shows a schematic layout of biohydrogen production setup. However, FIG. 3 shows the actual lab scale setup of CSTR 12 that was operated for 30 days continuously with a continuous production of biohydrogen.

Results and Discussion: Viability of Continuous Biohydrogen Generation

Figure 4:
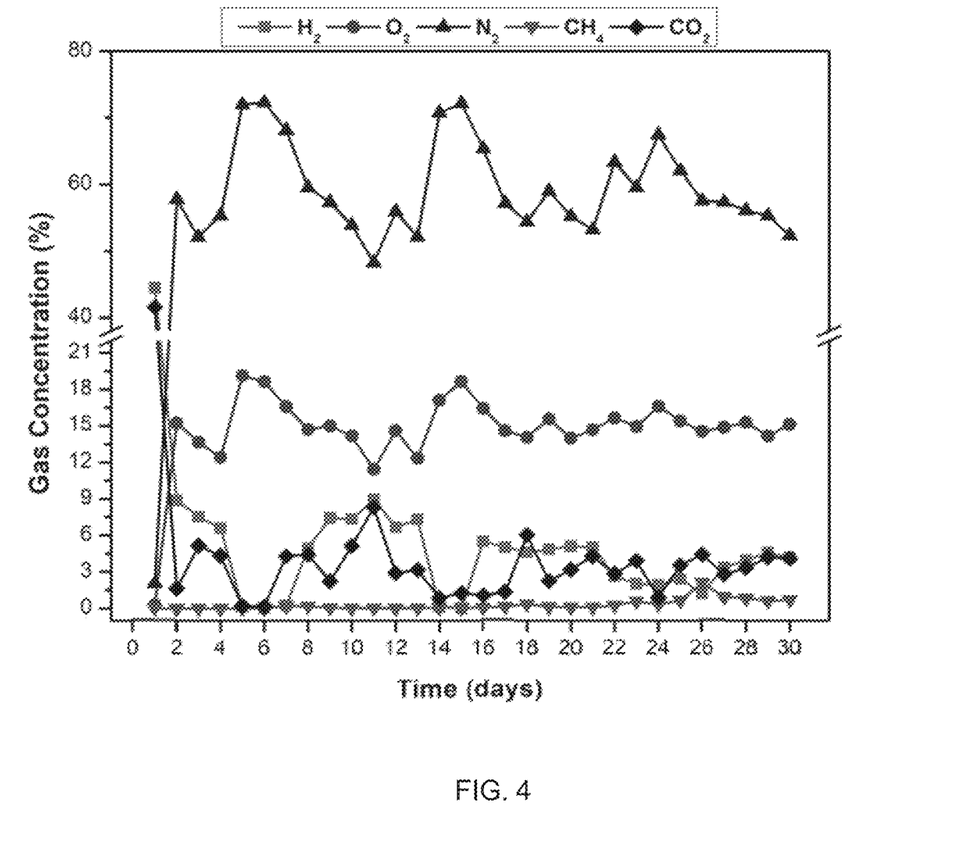
FIG. 4 shows a graph showing biohydrogen production using the apparatus and method of FIG. 3, showing gases concentration during an incubation period of 30 days.

The viability of continuous biohydrogen production in a CSTR 12 using the co-culture of WWAS and microalgae is shown in FIG. 4. The CSTR was run for a period of 30 days with a continuous flow of three separate streams of WWAS, microalgae (*C. vulgaris*), and nutrients with carbon substrate (glucose), respectively. It was observed that biohydrogen was continued to produce for a period of 30 days with the concentration ranging from 9-2% with respect to other gases in the biogas as shown in FIG. 4.

It was also observed that major portion of the biogas composition is nitrogen gas which is inert gas and varied from 70-48% followed by oxygen gas ranging from 19-11% as seen in FIG. 4. FIG. 4 shows that on day 5, 15, and 24, new inoculated microalgal medium was used as influent which raises the aerobic conditions inside the reactor and the resulting gas became rich in nitrogen and oxygen. Due to the increased level of oxygen, biohydrogen production was observed minimal on the same days as shown in FIG. 4. This indicates that biohydrogen and oxygen has inverse relation during CSTR operation. The maximum of 9% of biohydrogen was observed on day 11 during CSTR operation when oxygen and nitrogen was observed least during whole CSTR operation as 11% and 48%, respectively, as shown in FIG. 4. This indicates that biohydrogen concentration in final gas composition can be enhanced further by reducing the oxygen concentration up to the limiting value of 4-5%. Because further reduction in oxygen concentration might activate methanogenic activity which will start converting the biohydrogen produced into methane. The continuous production of biohydrogen in the current invention is regarded by the inventors as a breakthrough in the field of hydrogen energy that can be exploited further. Several factors and parametric modifications such as hydraulic retention time and flow rates can enhance the biohydrogen production potential. Higher retention time can increase the duration of microbial metabolism to extract the energy of organic biomass up to the peak limit.

Whereas slower flowrate might disable the continuous production of biohydrogen by not providing enough biomass and organic carbon for anaerobic fermentation. On the other hand, higher flowrates might not be able to stabilize and adapt the microbial community to the anaerobic environment for metabolism.

Effect of Total Organic Carbon (TOC) Concentration

The total organic carbon (TOC) is a parameter to estimate the amount of dissolved organic carbon present in the solution. The parameter reflects the amount of organic carbon required for anaerobic fermentation by bacterial community.

Figure 5:
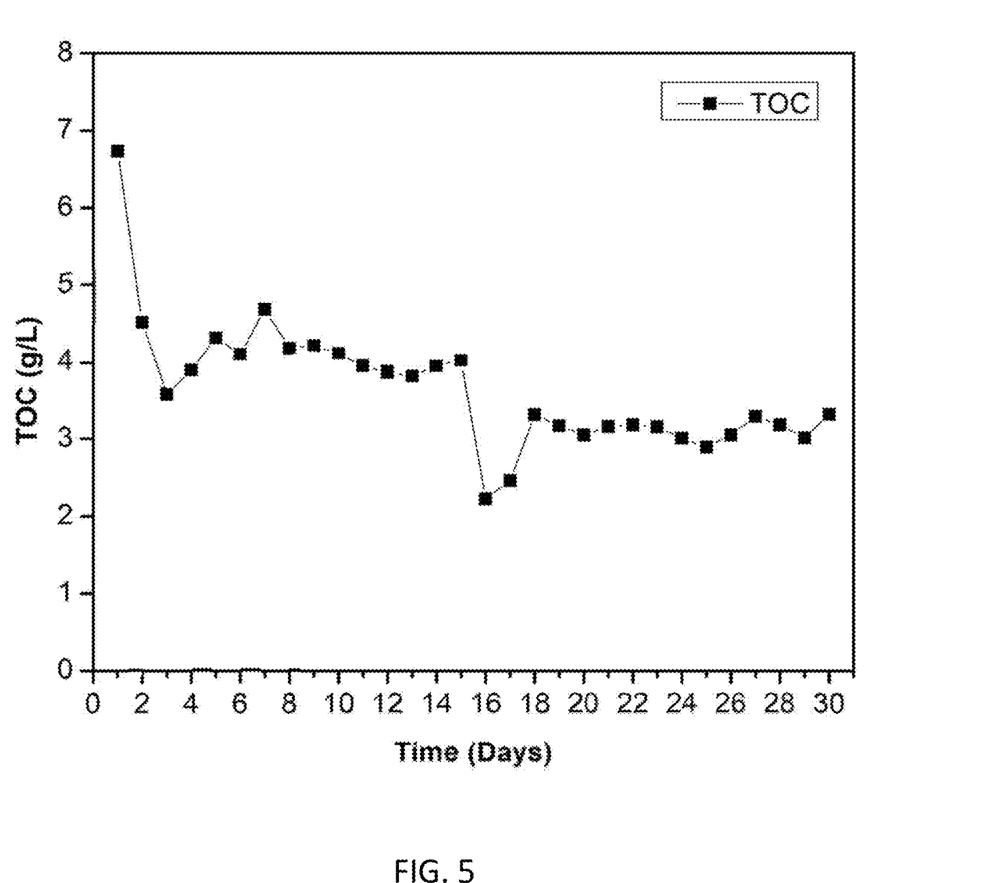
FIG. 5 shows a graph showing biohydrogen production using the apparatus and method of FIG. 3, showing total organic carbon (TOC) profile during biohydrogen production.

Usually, the anaerobic fermentation of organic carbon (glucose) generates hydrogen as end product at the end of fermentative metabolism. This hydrogen gets converted into methane during the methanogenic phase of fermentation in the presence of complete depletion of oxygen. Therefore, the samples from the reactor were accessed every day throughout the incubation period as shown in FIG. 5. It was observed that TOC concentration was decreased with the passage of days during incubation period. TOC concentration started from 6.7 g/L on the first day and stabilized at around 4 g/L until day 15 due to the continuous influent. At day 15, new microalgal medium was prepared which increased oxygen content, as shown in FIG. 4, due to which anaerobic conditions modified resulting in a sharp dip in TOC content. Afterwards, TOC stabilized at around 3.5 g/L which indicates the continuity of biohydrogen production and microbial activity in the reactor. This also predicts that chemical oxygen demand (COD) will also be reduced in the effluent with the reduction in TOC.

Therefore, the process can generate biohydrogen as well as can treat the wastewater with high organic content.

Advantages

The inventors have advantageously found that the method and apparatus of the invention can produce continuous biohydrogen using a CSTR 12 which is advantageous over biohydrogen produced in batch mode.

The present invention can furthermore reduce environmental impact of greenhouse gas emissions due to methane and carbon dioxide production, in accordance with the present invention these are only produced in traces. More specifically, the method and apparatus of the invention can produce energy rich non-hazardous gases (biohydrogen, oxygen, and nitrogen) with trace amount of greenhouse gases (carbon dioxide and methane).

The use of waste resources such as wastewater and food waste in the current invention can reduce the biohydrogen cost production as compared to the previous efforts. The system requires less energy inputs as microalgae can be photosynthetically grown and WWAS can be acquired from any wastewater treatment plant.

The inventors envisage that the Biohydrogen separation/purification from other gases is necessary. The invention is economically and practically feasible at pilot scale and large-scale applications for a continuous generation of biohydrogen.

The inventors envisage that the end product effluent is rich in volatile fatty acids that can be extracted and reutilized for microbial growth.

The inventors have further found that the apparatus and method in accordance with the invention is highly beneficial for the following reasons.

Figure 6:
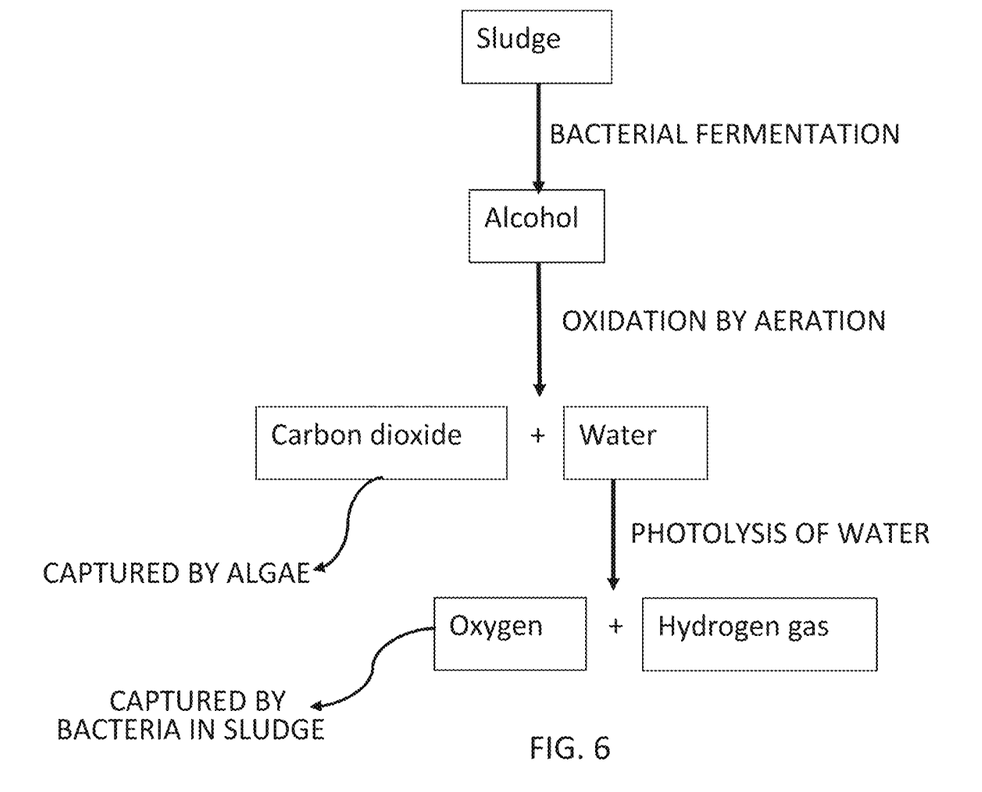
FIG. 6 shows a schematic overview of the biohydrogen production process produced by the apparatus and method, in accordance with the invention.
Figure 7:
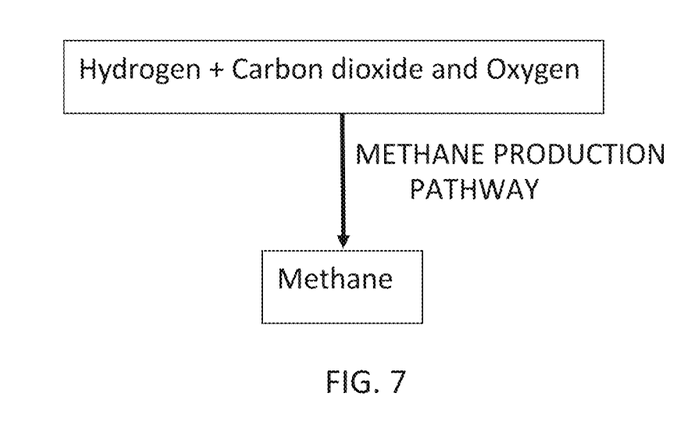
FIG. 7 shows a methane production process which is ameliorated using the apparatus and method, in accordance with the invention.

Referring to FIGS. 6 and 7 of the drawings, biohydrogen is generated inside CSTR 12 via anaerobic fermentation of sugar present in the influent and the organic matter present in WWAS. The microalgae, on the other hand, make sure the presence of minimal amount of oxygen to avoid further biohydrogen conversion into methane.

Many factors such as hydraulic retention time, flowrates, intensity of light, and availability of biodegradable organic matter can enhance biohydrogen content in the final gas composition. The inventors have developed a method 100 and apparatus 101 that can continuously produce biohydrogen with reduced greenhouse gas emissions. The setup can also be applicable at pilot scale at any wastewater treatment plant with a continuous stream of activated sludge.

The inventors have advantageously found that the use of natural organic waste such as wastewater activated sludge or food waste rich in organic matter and photosynthetically grown microalgae can reduce the cost of biohydrogen production via fermentation. Moreover, using the co-culture of organic waste and microalgae maintains a low level of oxygen that inhibits the conversion of biohydrogen into methane which is a greenhouse gas. This invention involves a continuous stirred tank reactor (CSTR 12) that can generate a continuous biohydrogen gas using a co-culture of wastewater activated sludge (WWAS) and photosynthetically grown microalgae (*Chlorella vulgaris*). The co-culture contains carbon substrates and nutrients essential for microalgal growth and anaerobic fermentation. The wastewater activated sludge provides high organic content for anaerobic fermentation. Whereas, different species of microalgae have different biohydrogen production potential, one of them reported for higher biohydrogen yield is *Chlorella vulgaris* (*C. vulgaris*). The maximum biohydrogen production potential by *C. vulgaris* and WWAS is reported as 1246 mL H2/L during a batch experiment.

The microalgae keep growing photosynthetically in the presence of light by producing oxygen, while the bacterial community present in WWAS serves the purpose of oxygen consumption and anaerobic fermentation of organic matter. Therefore, the CSTR 12 was designed with three separate continuous streams of microalgae, WWAS, and nutrients with carbon substrate that can produce a continuous flow of biogas. The major constituent of biogas is biohydrogen, oxygen, nitrogen, and traces of carbon dioxide.

The biohydrogen is a clean and sustainable biofuel, oxygen is necessary for living microorganisms, nitrogen is an inert gas contains no harmful effects, and carbon dioxide is considered as less harmful gas produced in minimal volume. The current innovative setup can be placed outdoor in any wastewater treatment plant with a stream of activated sludge directly from the effluent of secondary tank. Microalgal stream can be sourced from outdoor microalgal pond. The use of real WWAS from wastewater treatment plant is encouraged in this innovative technique because the WWAS contains a diverse bacterial community for anaerobic fermentation. In contrast, the use of mono bacterial strain in the previous studies requires a contaminated free environment to maintain the purity of bacterial strain which is an expensive and laborious technique. Further, the use of waste resource such as WWAS is utilized to generate green energy. The effluent of CSTR is rich in volatile fatty acids that can be further extracted and exploited in various purposes. The residue hereafter can be dumped on an open land to dry and use as dry biomass.

The inventors have particularly found that the apparatus 101 and method 100, in accordance with the invention, is particularly advantageous because, by keeping the microorganism inlet stream 22.1, an organic waste inlet stream 22.2, and the nutrient inlet stream 22.3 separated from one another before controlled mixing in the bioreactor chamber 20, methanogenic activity is highly reduced and avoided as described and defined hereinabove and as shown in FIGS. 6 and 7 of the drawings.

The inventors have particularly found that the apparatus 101 and method 100, in accordance with the invention, is particularly advantageous because the apparatus permits pH, flowrates, retention time, oxygen concentration, gas accumulation, and effluent to be regulated simultaneously, in order to enhance biohydrogen production and particularly, inhibit the conversion of biohydrogen into biomethane. More particularly, because of the separate microorganism inlet stream 22.1, an organic waste inlet stream 22.2, and the nutrient inlet stream 22.3, the volume and flow rate of *Chlorella vulgaris*, WWAS and nutrients, can be actively regulated to maximize biohydrogen production and specifically inhibit the production of methane so as to favour biohydrogen production.

The exact configuration of the apparatus 101 and method 110, in accordance with the invention, may vary greatly while still incorporating the essential features of the invention as described hereinabove.

The invention extends to the apparatus 101 defined and described hereinabove including the inlet streams and/or the outlet stream. The invention extends also to the use of the apparatus 101 defined and described hereinabove.

The invention claimed is:

1. An apparatus for producing a stream of biohydrogen, the apparatus including:
   a continuous flow bioreactor having:
   (a) an internal bioreactor chamber having a sidewall without any gas permeable porous material;
   (b) three separate inlet streams, each inlet stream leading into the bioreactor chamber; and
   (c) an outlet stream leading out of the bioreactor chamber and through which the contents of the bioreactor chamber can flow out of the bioreactor chamber;
   a fluid flow controlling means for independently and continuously controlling a fluid flow through the associated inlet stream for controlling fluid flow via the associated inlet stream into the bioreactor chamber;
   wherein the inlet streams comprise:
   (i) a photosynthesizing microorganism inlet stream;
   (ii) an organic waste inlet stream; and
   (iii) a nutrient inlet stream;
   and a lighting means for exposing the photosynthesizing microorganism to light, thereby to enable photosynthesis;
   wherein the fluid flow controlling means is operable for controlling one or more of the hydraulic retention time and the flow rates through the bioreactor for enhancing biohydrogen production.

2. The apparatus as claimed in claim 1, wherein the stream of biohydrogen is a continuous stream of biohydrogen.

3. The apparatus as claimed in claim 1, wherein the bioreactor has a stirring means for stirring the contents of the bioreactor chamber.

4. The apparatus as claimed in claim 1, wherein the bioreactor is in the form of a continuous flow stirred tank reactor (CSTR).

5. The apparatus as claimed in claim 1, wherein the photosynthesizing microorganisms is in the form of microalgae.

6. The apparatus as claimed in claim 1, wherein the microalgae is *Chlorella vulgaris*.

7. The apparatus as claimed in claim 1, wherein the organic waste sludge is in the form of wastewater activated sludge (WWAS).

8. The apparatus as claimed in claim 1, wherein the apparatus includes one or more ports in flow communication with the bioreactor chamber, wherein said one or more ports are selected from the group consisting of: a pH control port, a hydrogen sensor port, an oxygen sensor port, a gas collection port, a gas sensor port; and combinations thereof.

9. The apparatus as claimed in claim 1, wherein the fluid flow controlling means is further configured for controlling a fluid flow through the outlet stream for controlling fluid flow via the outlet stream out of the bioreactor chamber.

10. The apparatus as claimed in claim 9, wherein the fluid flow controlling means includes one or more of a photosynthesizing microorganism inlet stream controller; an organic waste inlet stream controller; a nutrient inlet stream controller; and an outlet stream controller; for controlling, respectively, a fluid flow through the photosynthesizing microorganism inlet stream; the organic waste inlet stream; the nutrient inlet stream; the outlet stream.

11. The apparatus as claimed in 10, wherein the fluid flow controlling means is operable for controlling one or more of the hydraulic retention time; and the flow rates through the bioreactor.

12. The apparatus as claimed in 11, wherein the photosynthesizing microorganism inlet stream controller; the organic waste inlet stream controller; the nutrient inlet stream controller; and the outlet stream controller is in the form of a photosynthesizing microorganism inlet pump; an organic waste inlet pump; a nutrient inlet stream pump; an outlet stream pump.

13. The apparatus as claimed in 1, wherein the lighting means is provided by a light transmittable sidewall defining the bioreactor chamber, and through which light may enter the bioreactor chamber.

14. The apparatus as claimed in 13, wherein the lighting means further includes one or more light source arranged for transmitting light via the light transmittable sidewall into the interior of the bioreactor chamber.

15. The apparatus as claimed in 14, wherein said one or more light source is in the form of a lamp.

16. The apparatus as claimed in claim 1, including the inlet streams.

17. The apparatus as claimed in claim 1, wherein the three separate inlet streams are for continuous inflow of influent.

18. The apparatus as claimed in claim 1, wherein the outlet stream is for continuous outflow of effluent.

19. The apparatus as claimed in claim 1, wherein the fluid flow controlling means is operable for reducing the oxygen concentration in the outlet stream to between 4% to 5%, thereby inhibiting conversion of biohydrogen into methane.

* * * * *